(12) United States Patent
Ramare et al.

(10) Patent No.: US 11,083,590 B2
(45) Date of Patent: Aug. 10, 2021

(54) INTERSOMATIC PROSTHESIS WITH LATERAL INTRODUCTION

(71) Applicant: ORTHOPAEDIC & SPINE DEVELOPMENT (OSD), Avignon (FR)

(72) Inventors: Stéphane Ramare, Le Mans (FR); Patrick Tropiano, Marseilles (FR); Paolo Mangione, Bordeaux (FR)

(73) Assignee: Orthopaedic & Spine Development (OSD), Avignon (FR)

( * ) Notice: Subject to any disclaimer, the term of this patent is extended or adjusted under 35 U.S.C. 154(b) by 0 days.

(21) Appl. No.: 16/830,914

(22) Filed: Mar. 26, 2020

(65) Prior Publication Data
US 2020/0306053 A1    Oct. 1, 2020

(30) Foreign Application Priority Data
Mar. 26, 2019   (FR) ...................................... 1903144

(51) Int. Cl.
*A61F 2/44*       (2006.01)
*A61F 2/30*       (2006.01)

(52) U.S. Cl.
CPC ............ *A61F 2/442* (2013.01); *A61F 2/4465* (2013.01); *A61F 2002/3008* (2013.01); *A61F 2002/30841* (2013.01)

(58) Field of Classification Search
CPC .......... A61F 2/44; A61F 2/442; A61F 2/4455; A61F 2/446; A61F 2/4465; A61F 2/447; A61F 2002/3008; A61F 2002/30187; A61F 2002/30261; A61F 2002/30266; A61F 2002/30841; A61F 2002/30904; A61F 2002/3093

See application file for complete search history.

(56) References Cited

U.S. PATENT DOCUMENTS

| | | | | |
|---|---|---|---|---|
| 7,060,073 | B2 * | 6/2006 | Frey ...................... | A61F 2/4611 606/85 |
| 7,918,891 | B1 * | 4/2011 | Curran .................. | A61F 2/4611 623/17.16 |
| 8,673,005 | B1 * | 3/2014 | Pimenta ................ | A61F 2/4455 623/17.11 |
| 9,351,845 | B1 * | 5/2016 | Pimenta ............ | A61B 17/0218 |
| 9,730,802 | B1 * | 8/2017 | Harvey ................ | A61F 2/4611 |

(Continued)

FOREIGN PATENT DOCUMENTS

WO    2005097004    10/2005

*Primary Examiner* — Eric S Gibson
(74) *Attorney, Agent, or Firm* — Burris Law, PLLC

(57) ABSTRACT

An intersomatic prosthesis with lateral introduction with a prosthesis body symmetrical along a sagittal plane is provided. The intersomatic prosthesis includes a convex anterior lateral wall along an anterior radius of curvature and a convex posterior lateral wall along a posterior radius of curvature larger than the anterior radius of curvature, a right end wall and a left end wall, and a lower bearing wall and an upper bearing wall open onto an inner space. The lower bearing wall has a central lower portion provided with lower teeth having lower bearing tips defining a lower bearing surface which is planar, and the upper bearing wall has a central upper portion provided with upper teeth having upper bearing tips defining an upper bearing surface which is convex.

19 Claims, 10 Drawing Sheets

(56) References Cited

U.S. PATENT DOCUMENTS

| | | | |
|---|---|---|---|
| 9,918,847 B2* | 3/2018 | Roussouly | A61F 2/442 |
| 10,322,008 B2* | 6/2019 | Seifert | A61F 2/4611 |
| 10,478,313 B1* | 11/2019 | Sweeney, III | A61F 2/447 |
| 2003/0181981 A1* | 9/2003 | Lemaire | A61F 2/4455 623/17.11 |
| 2006/0217806 A1* | 9/2006 | Peterman | A61F 2/447 623/17.11 |
| 2007/0208343 A1* | 9/2007 | Magerl | A61B 17/025 606/86 A |
| 2007/0260320 A1* | 11/2007 | Peterman | A61F 2/447 623/17.16 |
| 2009/0276049 A1* | 11/2009 | Weiland | A61F 2/4455 623/17.16 |
| 2011/0106259 A1* | 5/2011 | Lindenmann | A61F 2/4465 623/17.16 |
| 2011/0230970 A1* | 9/2011 | Lynn | A61F 2/4611 623/17.16 |
| 2014/0303736 A1* | 10/2014 | Roussouly | A61F 2/4465 623/17.16 |
| 2015/0100129 A1* | 4/2015 | Waugh | A61B 17/7059 623/17.16 |
| 2016/0051374 A1* | 2/2016 | Faulhaber | A61B 17/8023 623/17.15 |
| 2016/0113773 A1* | 4/2016 | Ganem | A61F 2/447 623/17.16 |
| 2016/0213486 A1* | 7/2016 | Nunley | A61F 2/4465 |
| 2017/0281360 A1* | 10/2017 | Seifert | A61F 2/4611 |
| 2020/0188130 A1* | 6/2020 | Jebsen | A61F 2/447 |
| 2020/0289288 A1* | 9/2020 | Muller | B33Y 80/00 |
| 2020/0306053 A1* | 10/2020 | Ramare | A61F 2/4455 |

\* cited by examiner

INTERSOMATIC PROSTHESIS WITH LATERAL INTRODUCTION

CROSS-REFERENCE TO RELATED APPLICATIONS

This application claims priority to and the benefit of FR 19/03144 filed on Mar. 26, 2019. The disclosure of the above application is incorporated herein by reference.

FIELD

The present disclosure relates to an intersomatic prosthesis with lateral introduction, in other words a spacing prosthesis for vertebral bodies.

More particularly, it concerns an intersomatic prosthesis designed so as to be introduced between two vertebral bodies, and more particularly between the vertebral bodies of thoracic or lumbar super- and sub-jacent vertebrae of a vertebral column, and whose geometry enables a customized setting of the lordosis angle that the surgeon wishes to impart to the vertebral segment.

Thus, the present disclosure concerns the technical fields of intersomatic prostheses, also called intersomatic cages, used in orthopedic surgeries of the vertebral column, in particular in the treatment of individuals suffering from a disc degeneration at the level of the thoracic or lumbar vertebrae.

The prosthesis according to the present disclosure is intended to be implanted in a lateral way (also called extraforaminal way), from the right or from the left, between two adjacent vertebral bodies in place of a defective disc, and more specifically to be implanted so as to provide the fusion between the vertebral bodies and thus allowing restoring the intra-disc height and especially recovering a customized physiological lordosis specific to the patient.

BACKGROUND

The statements in this section merely provide background information related to the present disclosure and may not constitute prior art.

It is known to use intersomatic prostheses to restore the intervertebral space (also called intersomatic space) between two adjacent vertebrae, by interposing at least one prosthesis in this intervertebral space and by promoting the formation of the solid bone bridge between the two adjacent vertebrae by means of a bone substitute internally carried by the prosthesis. To this end, a prosthesis conventionally has several peripheral walls including an upper wall and a lower wall intended to cooperate with the upper and lower vertebral endplates of the intervertebral space, in other words respectively the super- and sub-jacent lower and upper vertebrae delimiting the intervertebral space, and these lower and upper walls of the prosthesis are open onto an inner space of the prosthesis where a graft or a bone substitute is placed.

Amongst the intersomatic prostheses of the prior art, there are known, in particular from the documents US 2016/0278934, US 2015/0209153, US 2012/0158062, US 2015/0265420 and FR 2944692, intersomatic prostheses to be introduced laterally until being positioned between two vertebrae, astride a midplane of the vertebral column (or sagittal plane).

However, these prostheses of the prior art are hard to set in place, on the one hand because the passage along the lateral way towards the disc space is narrower than the disc space itself and, on the other hand, because there is no substantial risk of damaging the nervous tissues lying on either side of this passage. In order to avoid any incident during the introduction, these difficulties therefore force the surgeon to insert a prosthesis with smaller dimensions than those desired to adapt to the disc space. Thus, such undersized prostheses cannot provide a proper primary stability and the movability therefore creates a risk of pseudoarthrosis, without guaranteeing a proper arthrodesis.

The state of the art may also be illustrated by the teachings of the document U.S. Pat. No. 9,351,845 B1 which discloses an intersomatic prosthesis with lateral introduction which has a front wall forming a leading edge with beveled sidewalls for engagement between the vertebrae, and a rear wall forming a coupling support for an introduction tool, so that this prosthesis does not feature a sagittal symmetry. This prosthesis may be introduced both from a right approach way as well as from a left approach way, by turning the prosthesis and therefore by flipping its lower bearing wall and its upper bearing wall. The drawback lies in that these lower and upper bearing walls must be similar, in order to be able to flip them, which ultimately imposes shapes on these walls that are not optimum for the upper and lower vertebral endplates.

SUMMARY

This section provides a general summary of the disclosure and is not a comprehensive disclosure of its full scope or all of its features.

Hence, the present disclosure provides an intersomatic prosthesis with lateral introduction whose geometry allows for an easy lateral introduction, while offering an anatomical adaptation once in place on the upper and lower vertebral endplates.

According to one form of the present disclosure, an intersomatic prosthesis with lateral introduction which can be introduced both from a right approach and from a left approach is provided such that a bilateral introduction is provided by keeping its lower bearing wall turned downwards and its upper bearing wall turned upwards, while offering the desired anatomical properties between the upper and lower vertebral endplates. In other words, the introduction of the intersomatic prosthesis from the right or from the left is provided, and that without having to turn the prosthesis and without flipping its lower bearing wall and its upper bearing wall.

Thus, the present disclosure provides an intersomatic prosthesis with lateral introduction, such an intersomatic prosthesis comprising a prosthesis body symmetrical along a sagittal plane, extending along a longitudinal direction orthogonal to the sagittal plane, and comprising peripheral walls delimiting thereinside at least one inner space for receiving a bone substitute, these peripheral walls comprising:

two opposite lateral walls, respectively an anterior lateral wall and a posterior lateral wall, wherein the anterior lateral wall is convex along an anterior radius of curvature and the posterior lateral wall is convex along a posterior radius of curvature, this anterior radius of curvature being smaller than the posterior radius of curvature, and wherein the anterior lateral wall has in the sagittal plane an anterior height and the posterior lateral wall has in the sagittal plane a posterior height, this anterior height being larger than or equal to this posterior height;

two end walls, respectively a right end wall and a left end wall, extending symmetrically on either side of the sagittal plane;

two opposite bearing walls, respectively a lower bearing wall and an upper bearing wall, wherein the bearing walls has openings on the inner space, respectively a lower opening and an upper opening;

wherein:

the lower bearing wall successively has, between the right end wall and the left end wall, a right lower portion projecting from the right end wall and continuously extended by a central lower portion provided with lower teeth having lower bearing tips defining a lower bearing surface which is planar, and this central lower portion is extended by a left lower portion terminating in the left end wall;

the upper bearing wall successively has, between the right end wall and the left end wall, a right upper portion projecting from the right end wall and continuously extended by a central upper portion provided with upper teeth having upper bearing tips defining an upper bearing surface which is convex along an upper radius of curvature, and this central upper portion is extended by a left upper portion terminating in the left end wall;

the right lower portion and the right upper portion extend in a convergent manner in the direction of the right end wall, so that the prosthesis body has a right end including the right lower portion and the right upper portion, and wherein said right end has a height, measured between the right lower portion and the right upper portion, which decreases along the longitudinal direction starting from the central lower portion in the direction of the right end wall;

the left lower portion and the left upper portion extend in a convergent manner in the direction of the left end wall, so that the prosthesis body has a left end including the left lower portion and the left upper portion, and wherein said left end has a height, measured between the left lower portion and the left upper portion, which decreases along the longitudinal direction starting from the central lower portion in the direction of the left end wall.

With a symmetrical prosthesis body along a sagittal plane and which has symmetrically refined right and left ends, such an intersomatic prosthesis enables a bilateral introduction, that is to say a lateral introduction both from a right approach as well as from a left approach and that without having to flip its lower bearing wall and its upper bearing wall, while offering stability between the endplates once in place thanks to the geometry of the lateral walls and of the bearing walls.

Indeed, the intersomatic prosthesis in accordance with the present disclosure has a geometry of these different peripheral walls which provides an adaptation of the prosthesis between the two vertebrae, with an increase or a maximization of the contact surface between the lower and upper bearing walls of the intersomatic prosthesis and the adjacent vertebral endplates, and therefore an increase or a maximization of the contact surface of the bone substitute (also called bone graft) contained within the inner space of the prosthesis and these vertebral endplates, and also an enhanced primary stability of the intersomatic prosthesis for an improved arthrodesis.

The upper bearing wall has a toothed central upper portion which provides a convex upper bearing surface adapted for bearing on a lower face of the super-jacent vertebra (which forms an endplate called upper endplate) with a concave anatomy and thus having an advantageous effect of seamlessly distribute the forces over the upper bearing wall in contact with this upper endplate and therefore reducing the stresses that exert on the upper endplate, and thus reducing the risks of damaging the upper endplate and impinging the prosthesis in the vertebra.

In turn, the lower bearing wall has a toothed central lower portion which provides a planar lower bearing surface adapted for bearing on an upper face of the sub-jacent vertebra (which forms an endplate called lower endplate) with a substantially planar anatomy and thus having an improved distribution of the forces over the lower bearing wall in contact with this lower endplate and therefore reducing the stresses that exert on the lower endplate, and thus reducing the risks of damaging the lower endplate and impinging the prosthesis in the vertebra.

Moreover, the right and left ends are adapted, by being refined towards the right and left end walls, so as to bear on the cortical portions of the edges of the vertebrae, on either side of the sagittal plane, with the effect of distributing the compressive forces on these much more resistant portions of the vertebrae and therefore reducing the risk of impingement of the intersomatic prosthesis in the vertebral endplates by reducing the stresses on the central flexible portions of the endplates, and with a second effect of imparting a wedging of the prosthesis between the two vertebrae as the edges of the vertebrae close up, which provides an excellent stability of the intersomatic prosthesis.

According to one feature, the anterior radius of curvature is comprised between 30 and 70 millimeters, for example between 33 and 65 millimeters.

This anterior radius of curvature enables a considerable coverage of the surface of the vertebral endplates on the anterior side in accordance with the circular anterior anatomy of the vertebral bodies which have a substantially equivalent radius of curvature.

According to another feature, the posterior radius of curvature is comprised between 90 and 220 millimeters, for example between 100 and 210 millimeters.

This posterior radius of curvature allows reducing the risks of friction on the vascular and nervous tissues during the impingement and therefore the risk of compressing the dura mater when the intersomatic prosthesis is impinged.

According to one possibility, a ratio between the anterior radius of curvature and the posterior radius of curvature is comprised between 0.3 and 0.35.

Such a ratio is particularly adapted to address a wide range of anatomies and therefore a large number of patients.

According to another possibility, the upper radius of curvature is comprised between 90 and 160 millimeters, for example between 100 and 150 millimeters.

This upper radius of curvature allows for an optimum adaptation to the concave anatomy of the upper endplate for a distribution of the forces on the upper bearing wall.

Advantageously, the upper radius of curvature is comprised between 120 and 130 millimeters.

In a particular form, the lower opening opens into the lower bearing wall at least over the entirety of the length of the central lower portion, so that the lower teeth comprise, on either side of the lower opening, a row of anterior lower teeth adjacent to the anterior lateral wall and a row of posterior lower teeth adjacent to the posterior lateral wall, and wherein the upper opening opens into the upper bearing wall at least over the entirety of the length of the central upper portion, so that the upper teeth comprise, on either side of the upper opening, a row of anterior upper teeth adjacent to the anterior lateral wall and a row of posterior upper teeth adjacent to the posterior lateral wall.

Advantageously, the lower opening occupies between 50 and 75% of the surface area of the lower bearing wall, and the upper opening occupies between 50 and 75% of the surface area of the upper bearing wall.

Thus, these lower and upper openings occupy large proportions in the lower and upper bearing walls, thereby offering a wide contact area between the graft and the vertebral endplates.

In a particular form, the right lower portion and the right upper portion consist of planar portions extending in respective convergent planes, inclined at a right angle of inclination smaller than 45 degrees, so that the right end has a height which decreases in a linear manner along the longitudinal direction starting from the central lower portion in the direction of the right end wall;

and the left lower portion and the left upper portion consist of planar portions extending in respective convergent planes, inclined at a left angle of inclination equal to the right angle of inclination, so that the left end has a height which decreases in a linear manner along the longitudinal direction starting from the central lower portion in the direction of the left end wall.

Thus, these portions form at the ends of the inclined sidewalls which improve the introduction between the vertebral bodies, both from a right approach and from a left approach.

According to one possibility, the right angle of inclination and the left angle of inclination are comprised between 5 and 30 degrees.

According to another possibility, the right upper portion is provided with at least two projecting spikes, and the left upper portion is provided with at least two projecting spikes.

Such projecting spikes are intended to be fixed in the upper endplate, which results in locking the intersomatic prosthesis and thus inhibiting or preventing a displacement out of the intervertebral space. In other words, such projecting spikes form integrated anti-recoil devices.

According to one variant, the spikes project over a height comprised between 0.7 and 1.2 millimeters, for example between 0.8 and 1.0 millimeters.

In an advantageous form, the right end has a right slot opening both into the right end wall and into the two lateral walls and intended to cooperate with a gripping ancillary, and the left end has a left slot symmetrical to the right slot with respect to the sagittal plane and opening both into the left end wall and into the two lateral walls and also intended to cooperate with the gripping ancillary.

These slots forming recessed furrows on the perimeters of the ends of the intersomatic prosthesis for receiving a gripping ancillary adapted to safely handle the gripping prosthesis between the vertebral bodies during impingement.

According to one variant, the right slot extends, from the right end wall, into the posterior lateral wall over a posterior length and extends into the anterior lateral wall over an anterior length which is equal to or smaller than the posterior length, and the left slot extends, from the left end wall, into the posterior lateral wall over a posterior length and extends into the anterior lateral wall over the anterior length.

In a particular form, the anterior height is larger than or equal to the posterior height so that, in the sagittal plane, the upper bearing wall has a lateral inclination with respect to the lower bearing wall at a lateral angle of inclination which is comprised between 0 and 30 degrees.

According to one feature, the prosthesis body has four rounded edges at the junctures between the lateral walls and the bearing walls, said rounded edges extending longitudinally from the right end wall up to the left end wall following the respective curvatures of the lateral walls.

These rounded edges, which may for example be made in the form of connecting fillets, facilitate the introduction of the intersomatic prosthesis into the intervertebral space and reduce the risk of damaging the adjacent tissues, in particular the risks of hooking and breaking up the vessels of the lateral faces of the super- and sub-jacent vertebrae.

According to another feature, the intersomatic prosthesis comprises at least three markers made of a radiopaque material, with a right marker placed on the right end wall and a left marker placed on the left end wall asymmetrically to the right marker with respect to the sagittal plane, and further with a central marker placed on one of the lateral walls in the sagittal plane.

Such an arrangement of the three markers allows visualizing and therefore exactly monitoring the orientation of the intersomatic prosthesis in the three planes, namely the sagittal plane, the frontal plane and the horizontal plane.

According to another feature, an internal bridge extends inside the inner space between the two lateral walls, where this internal bridge is shifted downwards with respect to the upper bearing wall and is shifted upwards with respect to the lower bearing wall.

Thus, this internal bridge contributes to strengthening the intersomatic prosthesis, by reinforcing the internal space, while not affecting the contact surfaces that could be provided by the bone substitute. Indeed, because of the upward and downward shifts of this internal bridge, this internal bridge is not flush with the upper bearing wall and with the lower bearing wall, and thus the bone substitute can pass above this internal bridge (on the side of the upper bearing wall) and beneath the internal bridge (on the side of the lower bearing wall), and therefore offering maximized surfaces for contact with the upper and lower vertebral endplates.

According to another feature, a height, measured between the upper bearing wall and the lower bearing wall, decreases along the longitudinal direction, starting from the sagittal plane up to the right end wall, by 60 to 80%, and for example by about 75%, and symmetrically with respect to the sagittal plane, a height, measured between the upper bearing wall and the lower bearing wall, decreases along the longitudinal direction, starting from the sagittal plane up to the left end wall, by 60 to 80%, and for example by about 75%.

Such a decrease of the height participates to an advantageous refinement of the intersomatic prosthesis for a non-traumatic lateral introduction thereof, both from the right and from the left.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
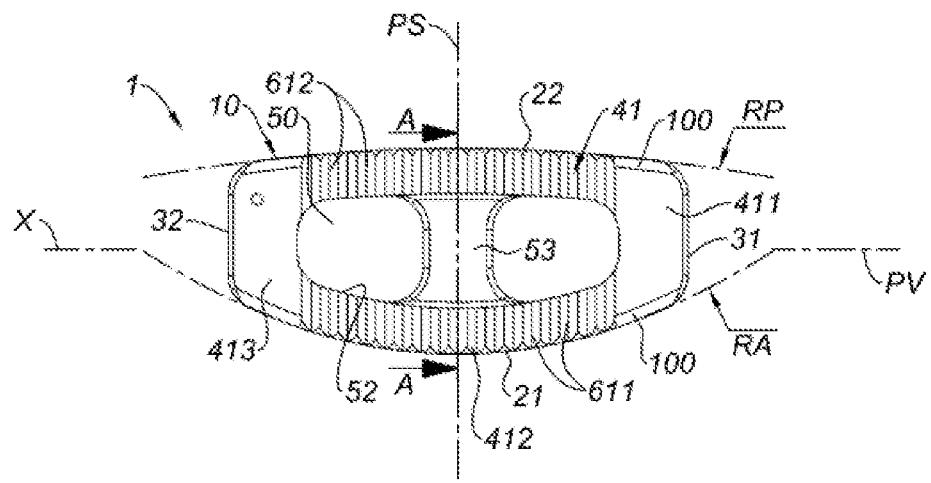
FIG. 1 is a bottom schematic view (view on the lower bearing face) of an intersomatic prosthesis according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Referring to FIGS. 1 to 12, an intersomatic prosthesis 1 with lateral introduction according to the present disclosure comprises a prosthesis body 10 symmetrical along a sagittal plane PS which, when in place, coincides with the sagittal plane of the vertebral column.

This prosthesis body 10 is made integrally in one-piece and its shape substantially matches with an ovoid or elongated parallelepiped. This prosthesis body 10 is made of a bio-implantable or biocompatible material, such as for example a polymer, titanium, a stainless steel alloy, a metal-polymer mixed alloy, a mineral or synthetic material. As a non-limiting example, the body is made of polyether ether ketone (PEEK), polyether ketone ketone (PEKK).

The prosthesis body 10 extends along a longitudinal direction X orthogonal to the sagittal plane PS and will coincide with its intervertebral introduction direction, in other words the guide direction of the lateral implantation thereof between the vertebral endplates PVI, PVS from the right or left side. This longitudinal direction X is contained in a horizontal plane PH, equivalent to the sectional plane B-B of FIG. 3, which is perpendicular to the sagittal plane PS. In the following description, a vertical plane PV, which contains the longitudinal direction X and which is perpendicular to both the sagittal plane PS and the horizontal plane PH, will also be considered.

The prosthesis body 10 comprises peripheral walls 21, 22, 31, 32, 41, 42 delimiting thereinside at least one inner space 5 for receiving a bone substitute, including:

two opposite lateral walls 21, 22, respectively an anterior lateral wall 21 and a posterior lateral wall 21, extending along the longitudinal direction and intended to extend substantially perpendicular to the lower and upper vertebral endplates PVI, PVS of an intervertebral space;

two end walls 31, 32, respectively a right end wall 31 and a left end wall 32, extending symmetrically on either side of the sagittal plane PS;

two opposite bearing walls 41, 42, respectively a lower bearing wall 41 and an upper bearing wall 42, where the lower bearing wall 41 is intended to bear against the lower vertebral endplate PVI and the upper bearing wall 42 is intended to bear against the upper vertebral endplate PVS.

The anterior lateral wall 21 is convex along an anterior radius of curvature RA comprised between 30 and 70 millimeters, for example between 33 and 65 millimeters.

The posterior lateral wall 22 is convex along a posterior radius of curvature RP which is larger than the anterior radius of curvature RA, and which is comprised between 90 and 220 millimeters, for example between 100 and 210 millimeters.

Thus, the two lateral walls 21, 22 are convex and therefore cambered outwardly from the prosthesis body 10.

Moreover, the anterior lateral wall 21 has in the sagittal plane PS an anterior height HA measured between the two bearing walls 41, 42, and the posterior lateral wall 22 has in the sagittal plane PS a posterior height HP, also measured between the two bearing walls 41, 42, and this anterior height HA is larger than the posterior height HP.

In general, the prosthesis body 10 has a height corresponding to the anterior height HA which is comprised between 5 and 20 millimeters, for example between 8 and 16 millimeters. Regardless of the height of the prosthesis body 10, the height difference between the two lateral walls 21, 22, namely the difference DH=HA−HP, is comprised between 0 and 9.0 millimeters, for example between 0.5 and 5.25 millimeters, so that, in the sagittal plane PS, the upper bearing wall 42 has a lateral inclination with respect to the lower bearing wall 41 at a lateral angle of inclination AL which is comprised between 0 and 30 degrees, for example between 0 and 18 degrees.

Complementarily, the prosthesis body 10 has a width LA corresponding to the distance between the two lateral walls 21, 22 measured in the sagittal plane and which is comprised between 16 and 24 millimeters, for example comprised between 18 millimeters and 22 millimeters. Furthermore, the prosthesis body 10 has a length LO (the distance between the end walls 31, 32 along the longitudinal direction X) comprised between 35 and 60 millimeters.

The lower bearing wall 41 has a lower opening 51 which opens onto the inner space 50 and the upper bearing wall 42 has an upper opening 52 which opens onto the inner space 50.

These openings 51, 52 have an oblong shape and extend along the longitudinal direction over at least half the overall length of the prosthesis body 10.

The lower opening 51 occupies between 50 and 75% of the surface area of the lower bearing wall 41, and the upper opening 52 occupies between 50 and 75% of the surface area of the upper bearing wall 42.

As shown in the figures, there is provided an internal bridge 53 extending inside the inner space 50 between the two lateral walls 21, 22; this internal bridge 53 being located in the sagittal plane PS. This internal bridge 53 extends substantially at mid-height between the two bearing walls 41, 42, so that this internal bridge 53 is shifted downwards with respect to the upper bearing wall 42 and is shifted upwards with respect to the lower bearing wall 41.

The lower bearing wall 41 successively has, between the right end wall 31 and the left end wall 32:
a right lower portion 411 projecting from the right end wall 31;
a central lower portion 412 which continuously extends the right lower portion 411 and which is provided with lower teeth 611, 612; and
a left lower portion 413 which continuously extends the central lower portion 412 and which terminates in the left end wall 32, where this left lower portion 413 is symmetrical to the right lower portion 411 with respect to the sagittal plane PS.

On the central lower portion 412, the lower teeth 611, 612 have lower bearing tips (also called free ends or spikes of the lower teeth 611, 612) which define a lower bearing surface SAI which is planar. In other words, the lower bearing tips of these lower teeth 611, 612 extend in the same plane thereby forming a planar lower bearing surface SAI intended to bear against the lower vertebral endplate PVI. It should be noted that this lower bearing surface SAI is inclined in the sagittal plane PS with respect to the horizontal plane PH because of the height difference DH described hereinabove.

All of the lower teeth 611, 612 have the same height, so that all of these lower teeth 611, 612 project from the same plane, parallel to the lower bearing surface SAI. These lower teeth 611, 612 have a height advantageously comprised between 0.7 and 1.2 millimeters, for example between 0.8 and 1.0 millimeters.

These lower teeth 611, 612 are symmetrical teeth bordered by two sidewalls extending symmetrically on either side of their respective lower bearing tips, and with apex angles comprised between 70 and 120 degrees, for example 90 degrees. The lower teeth 611, 612 form rectilinear teeth oriented along directions parallel to the sagittal plane PS, so that all of their lower bearing tips extend parallel to the sagittal plane PS.

Figure 2:
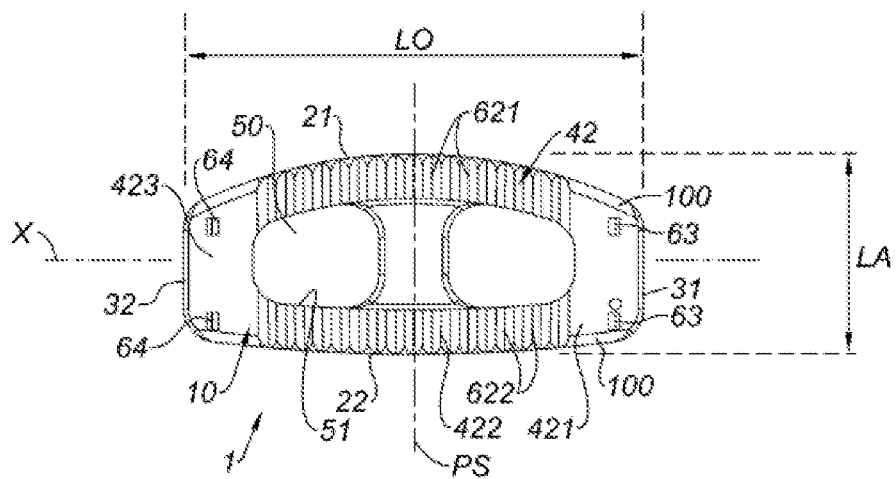
FIG. 2 is a top schematic view (view on the upper bearing face) of the intersomatic prosthesis of FIG. 1.
Figure 3:
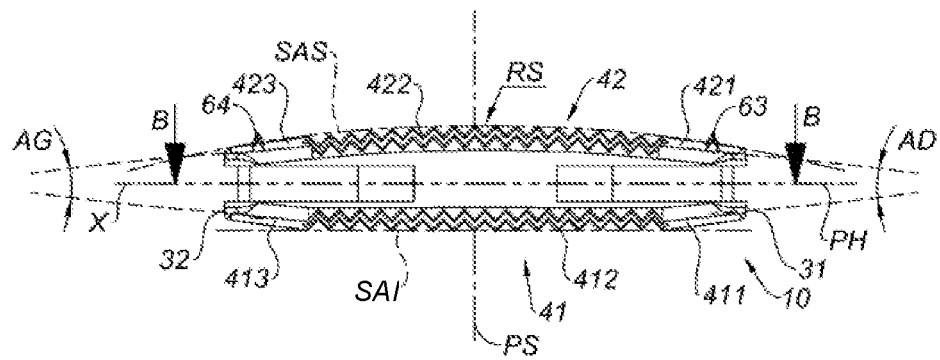
FIG. 3 is a schematic view of the posterior side (view on the posterior lateral face) of the intersomatic prosthesis of FIGS. 1 and 2.
Figure 4:
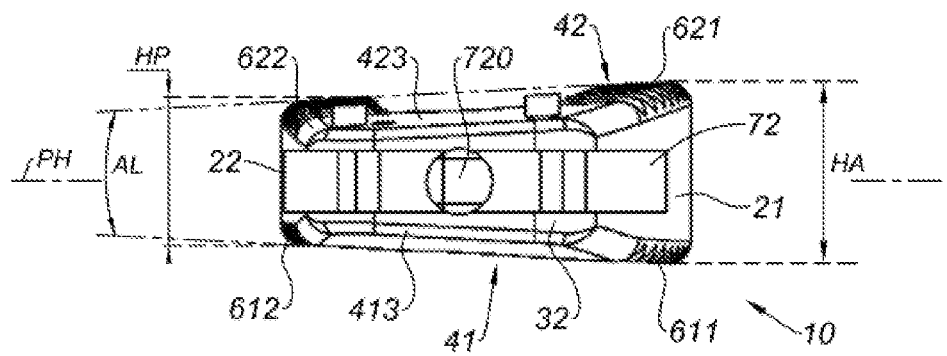
FIG. 4 is a schematic view of the left side (view on the left end face) of the intersomatic prosthesis of FIGS. 1 to 3.
Figure 5:
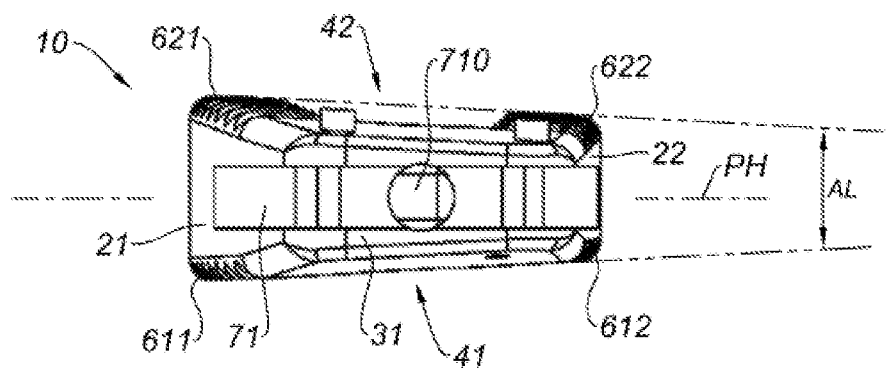
FIG. 5 is a schematic view of the right side (view on the right end face) of the intersomatic prosthesis of FIGS. 1 to 4.
Figure 6:
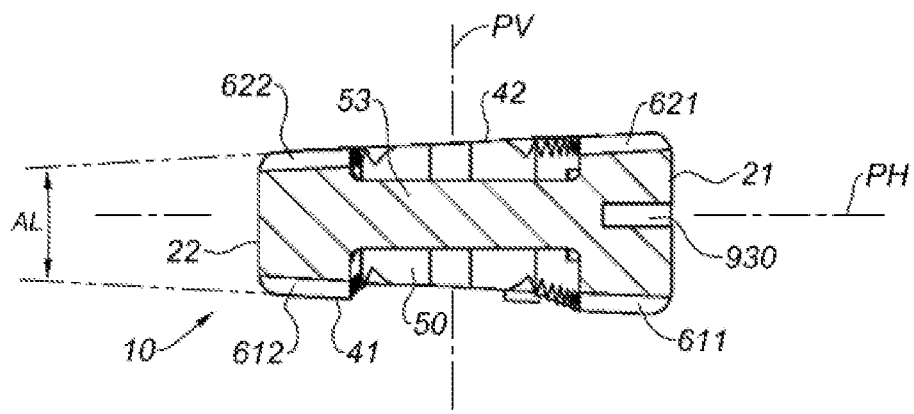
FIG. 6 is a sagittal sectional schematic view of the intersomatic prosthesis of FIGS. 1 to 5, along the sectional plane A-A visible in FIG. 1 corresponding to the sagittal plane.

As shown in FIG. 2, the lower opening 51 opens into the lower bearing wall 41 over at least the entirety of the central lower portion 412, so that the lower teeth 611, 612 comprise, on either side of the lower opening 51, a row of anterior lower teeth 611 adjacent to the anterior lateral wall 21 and a row of posterior lower teeth 612 adjacent to the posterior lateral wall 22.

The right lower portion 411 is a planar and smooth portion, extending in the continuation of the lower bearing surface SAI defined by the lower bearing tips of the lower teeth 611, 612, and that in an inclined manner in the vertical plane PV with respect to the horizontal plane PH (and also with respect to the lower bearing surface SAI) in the direction of a reduction of the height along the longitudinal direction X starting from the central lower portion 412 in the direction of the right end wall 31. It should be noted that this right lower portion 411 is also inclined in the sagittal plane PS with respect to the horizontal plane PH because of the height difference DH described hereinabove.

The left lower portion 413 is a planar and smooth portion, extending in the continuation of the lower bearing surface SAI, and that in an inclined manner in the vertical plane PV with respect to the horizontal plane PH (and also with respect to the lower bearing surface SAI) in the direction of a reduction of the height along the longitudinal direction X starting from the central lower portion 412 in the direction of the left end wall 32. It should be noted that this left lower portion 413 is also inclined in the sagittal plane PS with respect to the horizontal plane PH because of the height difference DH described hereinabove.

The upper bearing wall 42 successively has, between the right end wall 31 and the left end wall 32:
a right upper portion 421 projecting from the right end wall 31;
a central upper portion 422 which continuously extends the right upper portion 421 and which is provided with upper teeth 621, 622; and
a left upper portion 423 which continuously extends the central upper portion 422 and which terminates in the left end wall 32, where this left upper portion 423 is symmetrical to the right upper portion 421 with respect to the sagittal plane PS.

On the central upper portion 422, the upper teeth 621, 622 have upper bearing tips (also called free ends or apices of the upper teeth 621, 622) which define an upper bearing surface SAS which is convex along an upper radius of curvature RS which is comprised between 90 and 160 millimeters, for example between 100 and 150 millimeters and between 120 and 130 millimeters. In other words, the upper bearing tips of these upper teeth 621, 622 extend in the same convex fictional surface thereby forming a convex upper bearing surface SAS intended to bear against the upper vertebral endplate PVS. It should be noted that this upper bearing surface SAS is inclined in the sagittal plane PS with respect to the horizontal plane PH because of the height difference DH described hereinabove.

All of the upper teeth 621, 622 have the same height, so that all of these upper teeth 621, 622 project from the same surface which is convex along the same upper radius of curvature RS. These upper teeth 621, 622 has a height advantageously comprised between 0.7 and 1.2 millimeters, for example between 0.8 and 1.0 millimeters, and which is equivalent to that of the lower teeth 611, 612.

These upper teeth 621, 622 are symmetrical teeth bordered by two sidewalls extending symmetrically on either side of their respective upper bearing tips, and with apex angles comprised between 70 and 120 degrees, for example 90 degrees. The upper teeth 621, 622 form rectilinear teeth oriented along directions parallel to the sagittal plane PS, so that all of their upper bearing tips extend parallel to the sagittal plane PS.

As shown in FIG. 1, the upper opening 52 opens into the upper bearing wall 42 over at least the entirety of the central upper portion 412, so that the upper teeth 621, 622 comprise, on either side of the upper opening 52, a row of anterior upper teeth 621 adjacent to the anterior lateral wall 21 and a row of posterior upper teeth 622 adjacent to the posterior lateral wall 22.

The right upper portion 421 is a planar and smooth portion, extending in the continuation of the upper bearing surface SAS defined by the upper bearing tips of the upper teeth 621, 622, and that tangentially to the upper bearing surface SAS. Moreover, the right upper portion 421 is inclined in the vertical plane PV with respect to the horizontal plane PH in the direction of a reduction of the height along the longitudinal direction X starting from the central upper portion 422 in the direction of the right end wall 31. It should be noted that this right upper portion 421 is also inclined in the sagittal plane PS with respect to the horizontal plane PH because of the height difference DH described hereinabove. It should also be noted that this right upper portion 421 is symmetrical to the right lower portion 411 with respect to the horizontal plane PH.

Hence, the right lower portion 411 and the right upper portion 421 extend in a convergent manner in the direction of the right end wall 31, and more specifically the right lower portion 411 and the right upper portion 421 are planar portions extending in respective convergent planes, inclined in the vertical plane PV at a right angle of inclination AD smaller than 45 degrees, for example comprised between 5 and 30 degrees.

Thus, the prosthesis body 10 has a right end including the right lower portion 411 and the right upper portion 421, and this right end has a height, measured between the right lower portion 411 and the right upper portion 421, which decreases along the longitudinal direction starting from the central lower portion 412 (or of the central upper portion 422) in the direction of the right end wall 31. Advantageously, the height, measured between the upper bearing wall 42 and the lower bearing wall 41, decreases along the longitudinal direction X, starting from the sagittal plane PS up to the right end wall 31, by 60 to 80%, and for example by about 75%.

The left upper portion 423 is a planar and smooth portion, extending in the continuation of the upper bearing surface SAS, and that tangentially to the upper bearing surface SAS. Moreover, the left upper portion 423 is inclined in the vertical plane PV with respect to the horizontal plane PH in the direction of a reduction of the height along the longitudinal direction X starting from the central upper portion 422 in the direction of the left end wall 32. It should be noted that this left upper portion 423 is also inclined in the sagittal plane PS with respect to the horizontal plane PH because of the height difference DH described hereinabove. It should also be noted that this left upper portion 423 is symmetrical to the left lower portion 413 with respect to the horizontal plane PH.

Hence, the left lower portion 413 and the left upper portion 423 extend in a convergent manner in the direction of the left end wall 32, and more specifically the left lower portion 413 and the left upper portion 423 are planar portions extending in respective convergent planes, inclined in the vertical plane PV at a left angle of inclination AG smaller than 45 degrees, for example comprised between 5 and 30 degrees; this left angle of inclination AG being equivalent to the right angle of inclination AD because of the symmetry with respect to the sagittal plane PS. Advantageously, the height, measured between the upper bearing wall 42 and the lower bearing wall 41, decreases along the longitudinal direction X, starting from the sagittal plane PS up to the left end wall 32, by 60 to 80%, and for example by about 75%; this decrease being equivalent to that achieved on the right side because of the symmetry with respect to the sagittal plane PS.

Thus, the prosthesis body 10 has a left end including the left lower portion 413 and the left upper portion 423, and this left end has a height, measured between the left lower portion 413 and the left upper portion 423, which decreases along the longitudinal direction starting from the central lower portion 412 (or of the central upper portion 422) in the direction of the left end wall 32.

Hence, the prosthesis body 10 has right and left ends which are refined symmetrically on either side of the sagittal plane PS, so that the end walls 31, 32 have the same small heights in order to enable an easy introduction between the vertebral endplates PVI, PVS.

Moreover, it should be noted that the right upper portion 421 is provided with two projecting spikes 63, disposed on either side of the vertical plane PV. In an equivalent manner, the left upper portion 423 is also provided with two projecting spikes 64, disposed on either side of the vertical plane PV, these two spikes 64 being symmetrical to the spikes 63 with respect to the sagittal plane PS.

These spikes 63, 64 have projecting angles intended for an anterior-posterior and right-left lateral fastening in the upper vertebral endplate PVS, with the result of locking the intersomatic prosthesis 1 and inhibiting or preventing any migration out of the intersomatic space. These spikes 63, 64 project from the right and left upper portions 421, 423 over a height comprised between 0.7 and 1.2 millimeters, for example between 0.8 and 1.0 millimeters.

Furthermore, the prosthesis body 10 has four rounded edges 100 at the junctures between the lateral walls 21, 22 and the bearing walls 41, 42, therefore with a first rounded edge 100 between the anterior lateral wall 21 and the lower bearing wall 41, a second rounded edge 100 between the anterior lateral wall 21 and the upper bearing wall 42, a third rounded edge 100 between the posterior lateral wall 22 and the lower bearing wall 41, and finally a fourth rounded edge 100 between the posterior lateral wall 22 and the upper bearing wall 42. These rounded edges 100, which are in particular in the form of connecting fillets, extending longitudinally from the right end wall 31 up to the left end wall 32 following the respective curvatures of the lateral walls 21, 22, and therefore over the entirety of the length of the prosthesis body 10.

Moreover, the right end of the prosthesis body 10 has a right slot 71 opening both into the right end wall 31 and into the two lateral walls 21, 22. In an equivalent manner, the left end of the prosthesis body 10 has a left slot 72 opening both into the left end wall 32 and into the two lateral walls 21, 22; this left slot 72 being symmetrical to the right slot 71 with respect to the sagittal plane PS.

These two slots 71, 72 form two recessed furrows having a "U"-like general shape and which are intended to cooperate with a gripping ancillary 9, depending on the approach way. If the approach way is a right approach way, then the gripping ancillary 9 will cooperate with the right slot 71, and if the approach way is a left approach way, then the gripping ancillary 9 will cooperate with the left slot 72.

Figure 7:
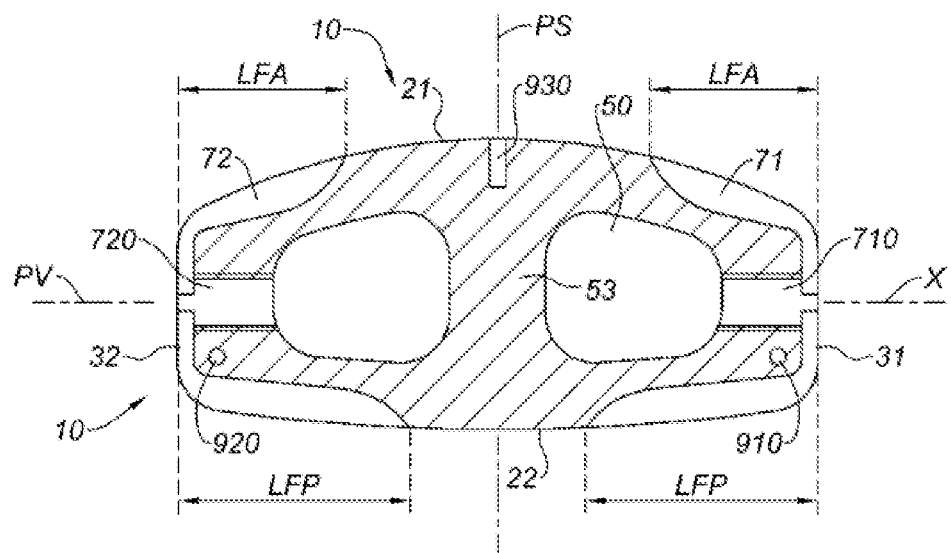
FIG. 7 is a horizontal sectional schematic view of the intersomatic prosthesis of FIGS. 1 to 6, along the sectional plane B-B visible in FIG. 3 corresponding to the horizontal plane.
Figure 8:
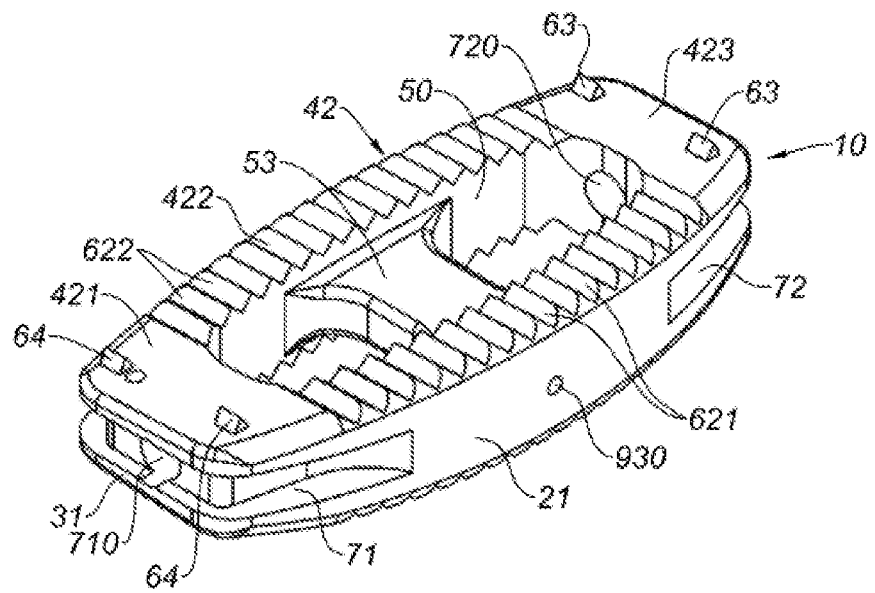
FIG. 8 is a perspective schematic view from the posterior and top side of the intersomatic prosthesis of FIGS. 1 to 7.
Figure 9:
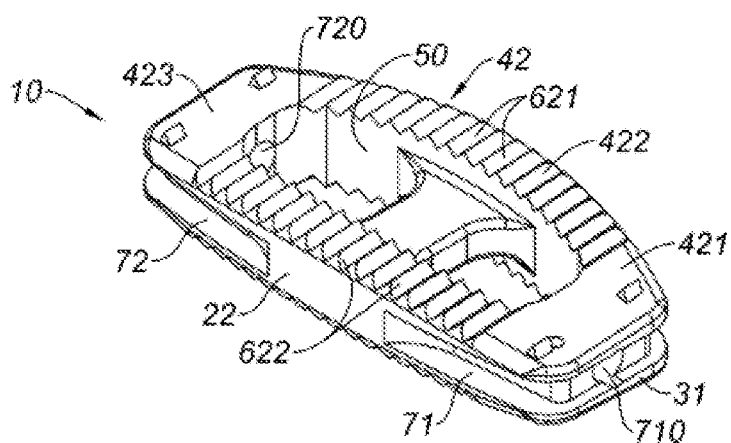
FIG. 9 is a perspective schematic view from the anterior and top side of the intersomatic prosthesis of FIGS. 1 to 8.
Figure 10:
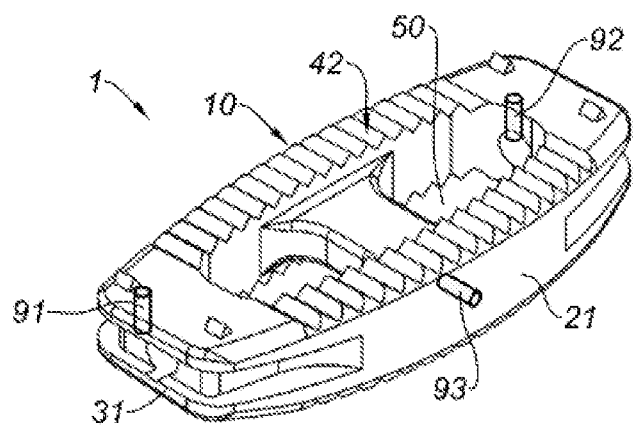
FIG. 10 is a perspective schematic view of the intersomatic prosthesis of FIGS. 1 to 9, with its prosthesis body shown transparent to visualize the three radiopaque material markers.
Figure 11:
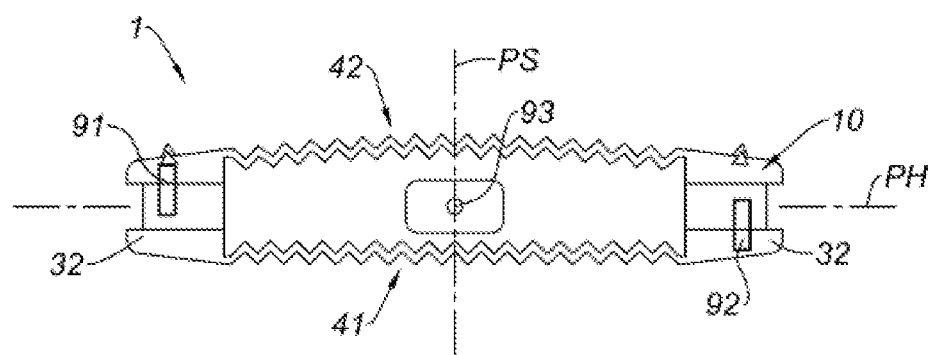
FIG. 11 is a schematic view of the posterior side of the intersomatic prosthesis of FIGS. 1 to 10, with its prosthesis body shown transparent to visualize the three radiopaque material markers.
Figure 15:
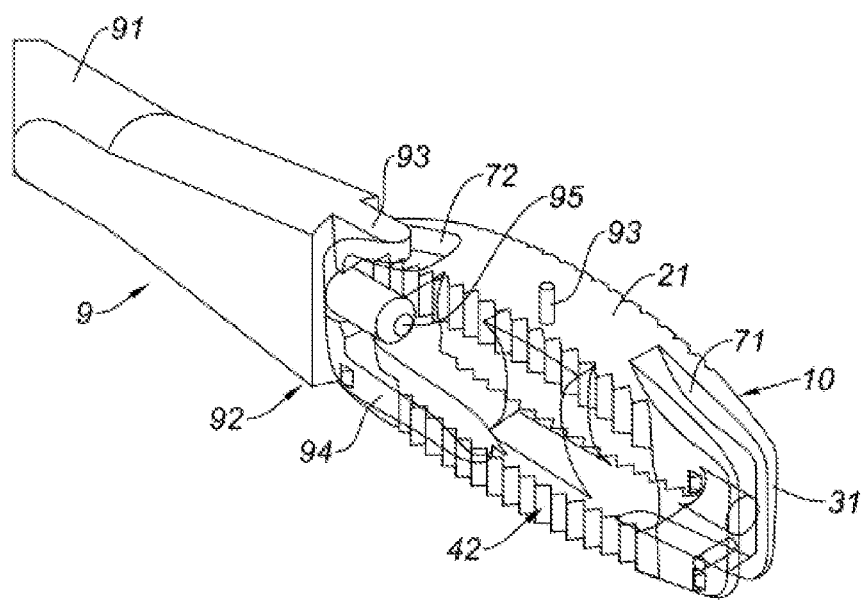
FIG. 15 is a perspective schematic view of the intersomatic prosthesis of FIGS. 1 to 12 held on the gripping ancillary of FIG. 13, with an enlarged view on the gripping head of the gripping ancillary and with the prosthesis body transparent.
Figure 16:
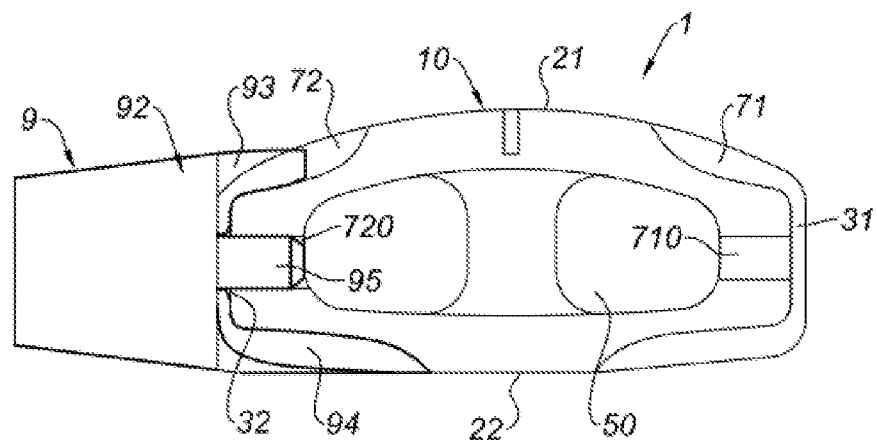
FIG. 16 is a top schematic view of the intersomatic prosthesis of FIGS. 1 to 12 held on the gripping ancillary of FIG. 13, with an enlarged view on the gripping head of the gripping ancillary and with the prosthesis body transparent.
Figure 17:
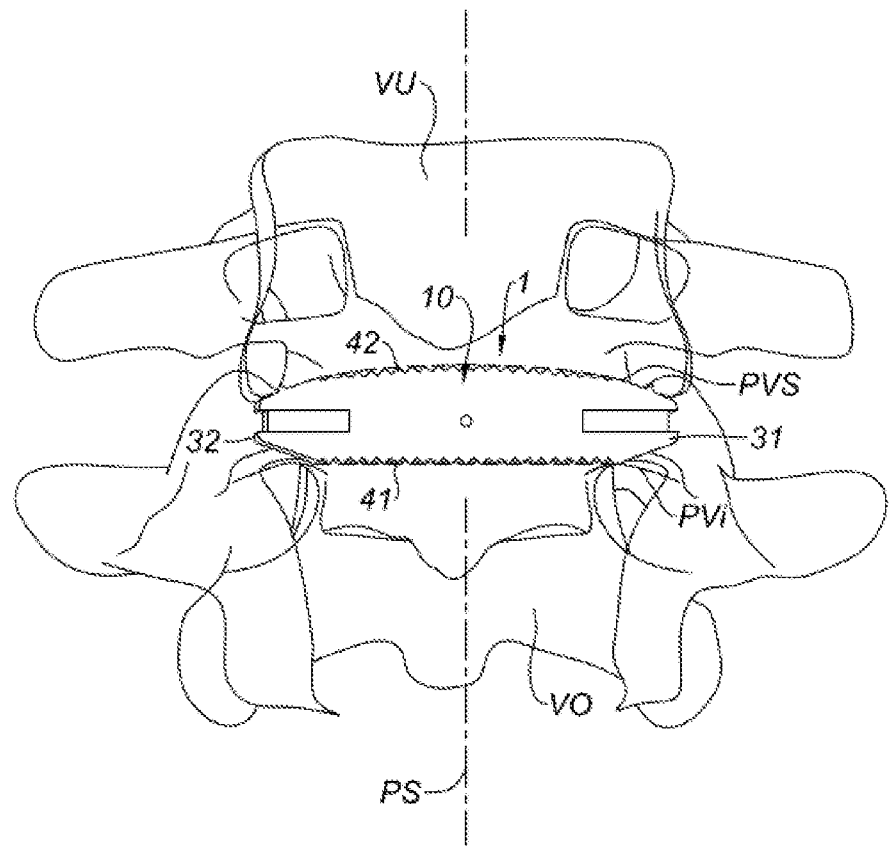
FIG. 17 is a schematic view of the anterior side of the intersomatic prosthesis of FIG. 1 to 12 in place between lower and upper vertebral endplates of an intervertebral space.
Figure 18:
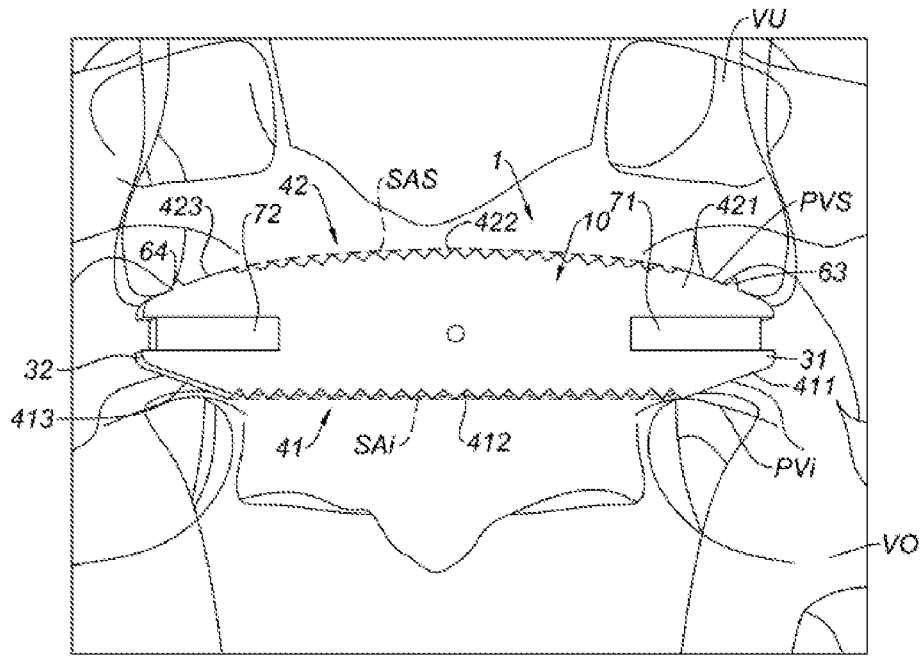
FIG. 18 is an enlarged schematic view of FIG. 17.
Figure 19:
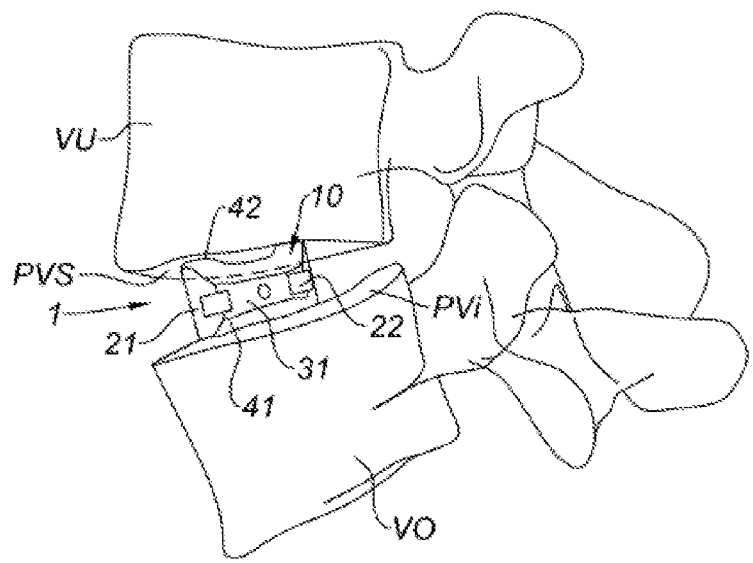
FIG. 19 is a schematic view of the right side of the intersomatic prosthesis of FIGS. 1 to 12 in place between lower and upper vertebral endplates of an intervertebral space.
Figure 20:
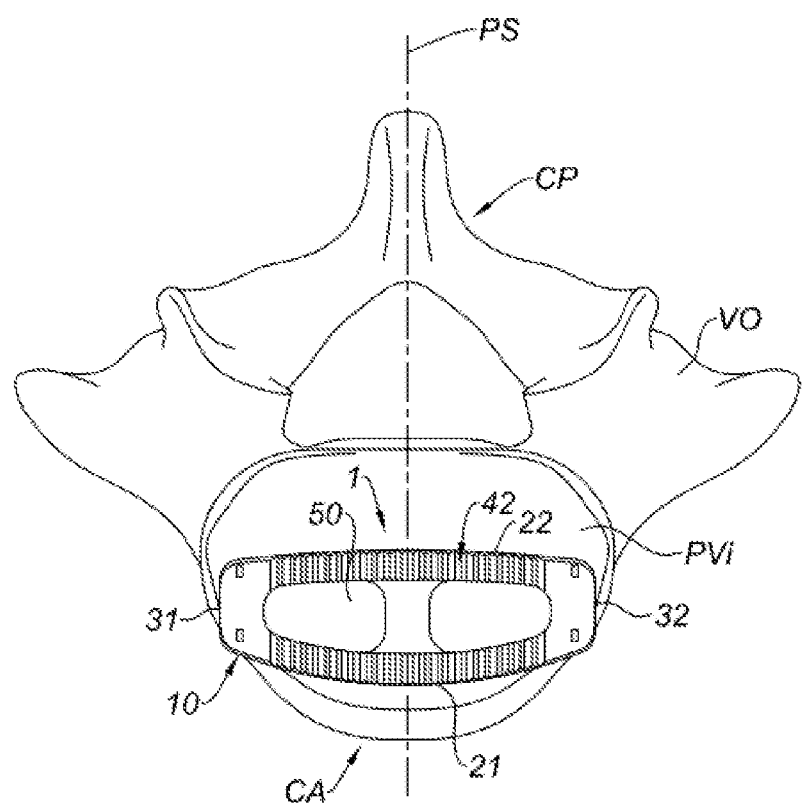
FIG. 20 is a top schematic view of the intersomatic prosthesis of FIGS. 1 to 12 in place on a lower vertebral endplate of an intervertebral space.

In the form shown in FIGS. 7, 15 and 16, it should be noted that the right slot 71 extends from the right end wall 31 over a larger length of the side of the posterior lateral wall 22 than the side of the anterior lateral wall 21. In other words, the right slot 71 extends, from the right end wall 31:

in the posterior lateral wall 22 over a determined posterior length LFP, and in the anterior lateral wall 21 over a determined anterior length LFA which is smaller than the posterior length LFP.

In an equivalent manner, the left slot 72 extends from the left end wall 32 over a larger length of the side of the posterior lateral wall 22 than the side of the anterior lateral wall 21. In other words, the left slot 72 extends, from the left end wall 32:

in the posterior lateral wall 22 over the aforementioned posterior length LFP, and in the anterior lateral wall 21 over the aforementioned anterior length LFA which is smaller than the posterior length LFP.

In a variant that is not illustrated, the right slot 71 extends from the right end wall 31 over the same length on the side of the posterior lateral wall 22 and on the side of the anterior lateral wall 21. In other words, the right slot 71 extends, from the right end wall 31:

in the posterior lateral wall 22 over a determined posterior length LFP, and in the anterior lateral wall 21 over a determined anterior length LFA which is equal to the posterior length LFP.

Also, still in this non-illustrated variant, the left slot 72 extends from the left end wall 32 over the same length on the side of the posterior lateral wall 22 and on the side of the anterior lateral wall 21. In other words, the left slot 72 extends, from the left end wall 32:

in the posterior lateral wall 22 over the aforementioned posterior length LFP, and in the anterior lateral wall 21 over the aforementioned anterior length LFA which is equal to the posterior length LFP.

There is also provided a right hole 710 formed in the right end wall 31 and extending along the longitudinal direction X, this right hole 710 opening into the right slot 71 and into the inner space 50. In an equivalent manner, there is also provided a left hole 720 formed in the left end wall 32 and extending along the longitudinal direction X, this left hole 720 opening into the left slot 72 and into the inner space 50; this left hole 720 being symmetrical to the right hole 710 with respect to the sagittal plane PS. These two holes 710, 720 are also intended to cooperate with the gripping ancillary 9.

For this purpose, and as illustrated in FIGS. 13 to 16, the gripping ancillary 9 comprises:

a handle 90 provided with an impingement surface 900 to allow impinging the gripping ancillary 9 and the intersomatic prosthesis 1;

a rod 91 extending the handle 90; and a gripping head 92 having a fork-like general shape adapted to cooperate with the prosthesis body 10.

This gripping head 92 is provided with:

an anterior arm 93 adapted to fit into the portion of the right or left slot 71, 72 which is formed in the anterior lateral wall 21;

a posterior arm 94 adapted to fit into the portion of the right or left slot 71, 72 which is formed in the posterior lateral wall 22;

a central stud 95, embedded between the two arms 93, 94, and which is adapted to fit inside the right or left hole 710, 720.

The anterior arm 93 is shorter than the posterior arm 94 because the anterior length LFA is smaller than the posterior length LFP, as explained hereinabove.

Alternatively, the anterior arm 93 is as long as the posterior arm 94, in particular if the anterior length LFA is equal to the posterior length LFP.

As shown in FIGS. 14 and 17 to 20, the intersomatic prosthesis 1 is intended to be implanted along, laterally (a right or left approach way) by means of the previously described gripping ancillary 9, between the upper vertebral endplate PVS and the lower vertebral endplate PVI of an intervertebral space, these vertebral endplates PVS, PVI being formed respectively by the lower face of a superjacent vertebra VU and by the upper face of a sub-jacent vertebra VO delimiting the intervertebral space (or intersomatic space).

Once in place, the lower bearing wall 41 bears against the lower vertebral endplate PVI and the upper bearing wall 42 bears against the upper vertebral endplate PVS, and the anterior lateral wall 21 is turned on the anterior side CA of the vertebral column whereas the posterior lateral wall 22 is turned on the posterior side CP of the vertebral column, with the sagittal plane PS of the prosthesis body 10 coincident or coplanar with the sagittal plane of the vertebral column.

In order to guide the positioning of the intersomatic prosthesis 1, it is advantageous that this intersomatic prosthesis 1 incorporates, on or within the prosthesis body 10, markers 91, 92, 93 made of a radiopaque material, for example three markers, namely:

a right marker 91 placed on the right end wall 31;

a left marker 92 placed on the left end wall 32 asymmetrically to the right marker 91 with respect to the sagittal plane PS; and a central marker 93 placed on any of the lateral walls 21, 22 in the sagittal plane PS.

All of the markers 91, 92, 93 are in the form of cylindrical studs 91, 92, 93, having a dimeter comprised between 1 and 2 millimeters and a length comprised between 2 and 5 millimeters.

Figure 12:
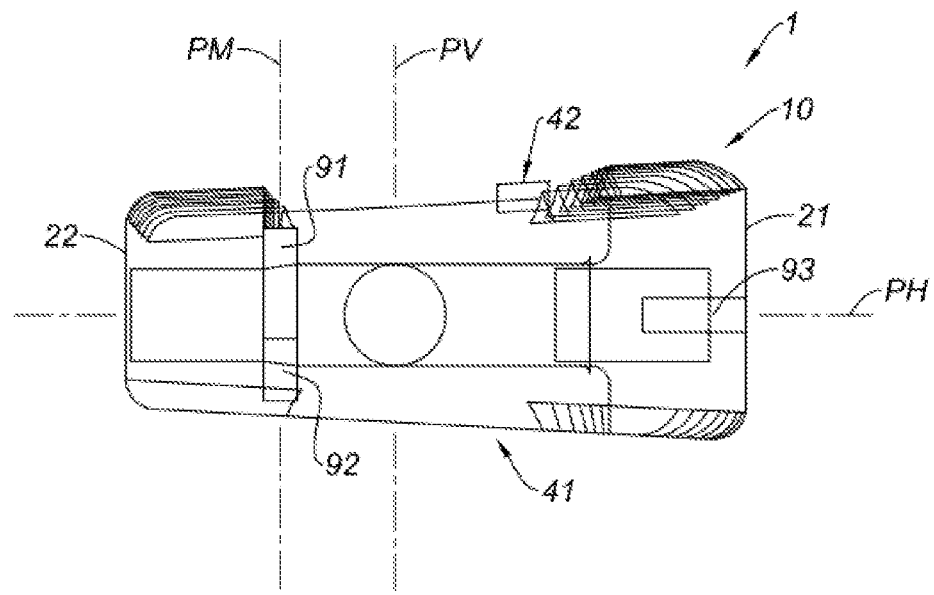
FIG. 12 is a schematic view of the left side of the intersomatic prosthesis of FIGS. 1 to 11, with its prosthesis body shown transparent to visualize the three radiopaque material markers.
Figure 13:
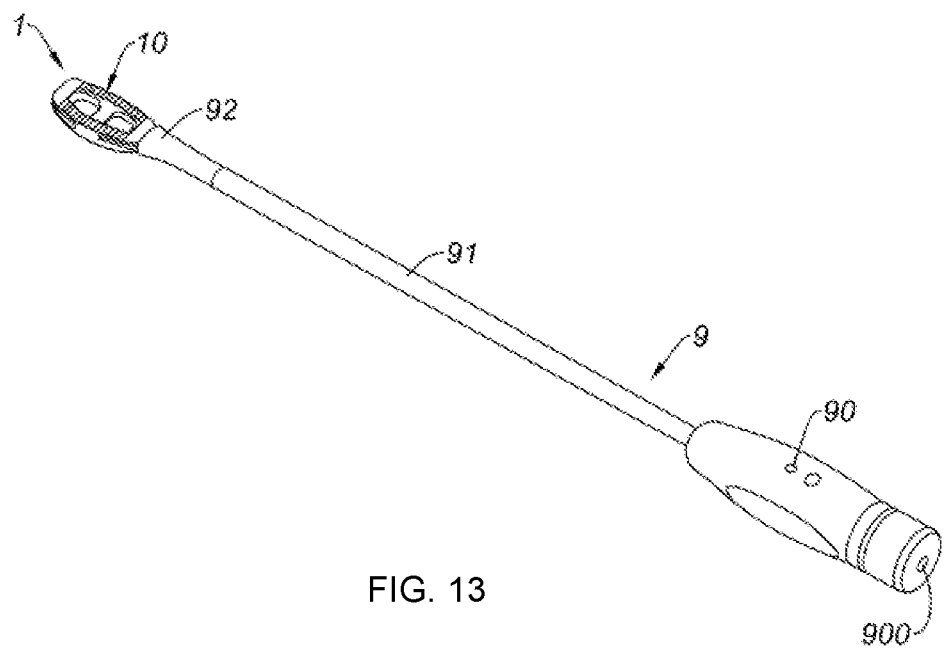
FIG. 13 is a perspective schematic view of the intersomatic prosthesis of FIGS. 1 to 12 held on a gripping ancillary.
Figure 14:
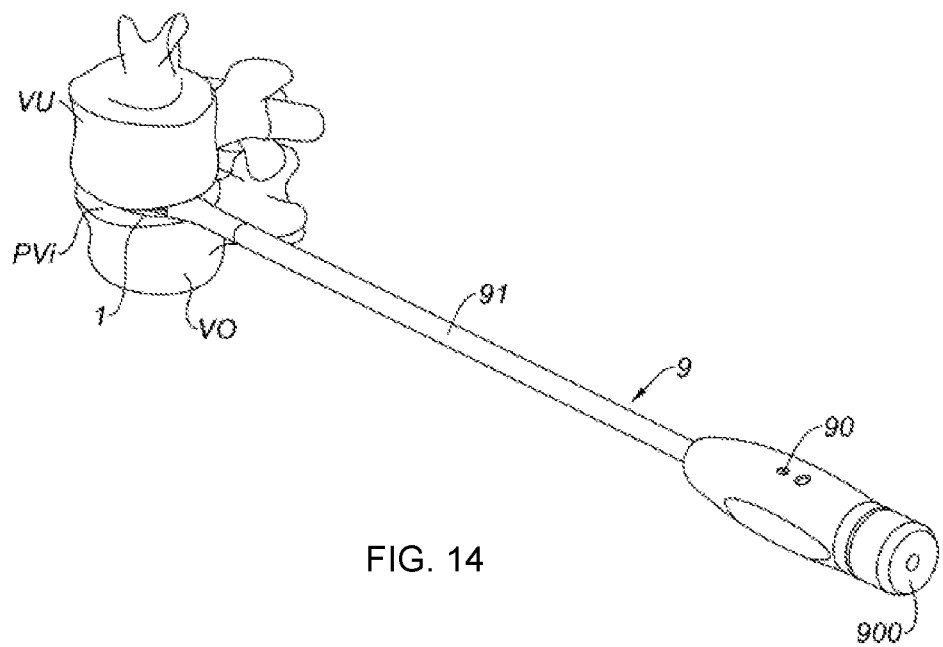
FIG. 14 is a perspective schematic view of the intersomatic prosthesis of FIGS. 1 to 12 held on the gripping ancillary of FIG. 13, during the introduction of the intersomatic prosthesis between lower and upper vertebral endplates of an intervertebral space, formed respectively by the upper and lower faces of the sub- and super-jacent vertebrae.

The right and left markers 91, 92 extend vertically and are disposed in the same plane PM parallel to the vertical plane PV, yet with the right marker 91 which is shifted upwards (and therefore closer to the upper bearing wall 42) whereas the left marker 91 is shifted downwards (and therefore closer to the upper bearing wall 42). Thus, and as shown in FIG. 12, viewed from the (right or left) side, the right and left markers 91, 92 are aligned and partially coincident, thereby allowing monitoring an orientation with respect to the horizontal plane PH or to the vertical plane PV. In turn, the central marker 93 extends horizontally, and perpendicular to the longitudinal direction X. In particular, it is disposed in the anterior lateral wall 21, at mid-height thereof.

All markers 91, 92, 93 are received into the orifices 910, 920, 930 formed in the prosthesis body 10 for the reception thereof, as shown in FIG. 7.

Hence, the previously described prosthesis 10 is remarkable in that the sagittal symmetry enables it to be advantageously implanted by a left or right approach way, while preserving properties of anatomical adaptation to the vertebral endplates PVI, PVS. The thinned left and right ends, associated to the rounded edges 100, enable a safe and non-traumatic impingement of the intersomatic prosthesis 1 during the penetration, these rounded edges 100 following the curvatures of the lateral walls 21, 22, thereby preserving the neurological and vascular structures located on the approach way on either side of the vertebrae VO, VU.

The intersomatic prosthesis 1 may be set in place from the left or the right; its positioning being achieved by means of the appropriate gripping ancillary 9, endoscopically or in "open surgery". Where desired, the intersomatic prosthesis 1 could be removed.

Hence, this intersomatic prosthesis 1 has a geometrically sophisticated design, but its implementation is simple and conforms perfectly to the shape of the vertebral endplates PVI, PVS without any risk of degradation of these vertebral endplates PVI, PVS, and which provides safety in particular thanks to its spikes 63, 64 forming anti-recoil devices, so as to provide a perfect primary stability (thanks to the teeth 611, 612, 621, 622) before osteosynthesis of the treated segment on the one hand and to optimally rectify a lordosis and/or a kyphosis on the other hand and thus improve the surgical treatment.

An advantage provided by this intersomatic prosthesis 1 lies in significantly reducing the risks of disc degeneration at the adjacent levels, known under the name of lumbosacral transitional vertebrae disc disease. Indeed, it is perfectly established that a balanced rebuild of the spinal column reduces or minimizes the forces and the actions of the muscles of the back but also of the legs because the patient does not make his body work to «straighten the spinal column» in the optimum position. The present intersomatic prosthesis 1 enables the surgeon to carry out a rebuild and to obtain a lordosis correction promoting an optimum sagittal balance, thereby reducing the risks of re-operation subsequent to a lumbosacral transitional vertebrae degeneration.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

The invention claimed is:

1. An intersomatic prosthesis for lateral introduction, said intersomatic prosthesis comprising: a prosthesis body symmetrical along a sagittal plane, extending along a longitudinal direction orthogonal to the sagittal plane, and comprising peripheral walls delimiting thereinside at least one inner space for receiving a bone substitute, said peripheral walls comprising:

two opposite lateral walls, respectively an anterior lateral wall and a posterior lateral wall, wherein the anterior lateral wall is convex along an anterior radius of curvature and the posterior lateral wall is convex along a posterior radius of curvature, said anterior radius of curvature being smaller than the posterior radius of curvature, and wherein the anterior lateral wall has in the sagittal plane an anterior height and the posterior lateral wall has in the sagittal plane a posterior height, said anterior height being larger than or equal to said posterior height;

two end walls, respectively a right end wall and a left end wall, extending symmetrically on either side of the sagittal plane;

two opposite bearing walls, respectively a lower bearing wall and an upper bearing wall, wherein the bearing walls have openings on the inner space, respectively a lower opening and an upper opening;

wherein:

the lower bearing wall successively has, between the right end wall and the left end wall, a right lower portion projecting from the right end wall and continuously extended by a central lower portion provided with lower teeth having lower bearing tips defining a lower bearing surface which is planar, said central lower portion is extended by a left lower portion terminating in the left end wall;

the upper bearing wall successively has, between the right end wall and the left end wall, a right upper portion projecting from the right end wall and continuously extended by a central upper portion provided with upper teeth having upper bearing tips defining an upper bearing surface which is convex along an upper radius of curvature, said central upper portion is extended by a left upper portion terminating in the left end wall;

the right lower portion and the right upper portion extend in a convergent manner in the direction of the right end wall, so that the prosthesis body has a right end including the right lower portion and the right upper portion, and wherein said right end has a height, measured between the right lower portion and the right upper portion, which decreases along the longitudinal direction starting from the central lower portion in the direction of the right end wall;

the left lower portion and the left upper portion extend in a convergent manner in the direction of the left end wall, so that the prosthesis body has a left end including the left lower portion and the left upper portion, and wherein said left end has a height, measured between the left lower portion and the left upper portion, which decreases along the longitudinal direction starting from the central lower portion in the direction of the left end wall.

2. The intersomatic prosthesis according to claim 1, wherein the anterior radius of curvature is between 30 and 70 millimeters.

3. The intersomatic prosthesis according to claim 1, wherein the posterior radius of curvature is between 90 and 220 millimeters.

4. The intersomatic prosthesis according to claim 1, wherein a ratio between the anterior radius of curvature and the posterior radius of curvature is between 0.3 and 0.35.

5. The intersomatic prosthesis according to claim 1, wherein the upper radius of curvature is between 90 and 160 millimeters.

6. The intersomatic prosthesis according to claim 5, wherein the upper radius of curvature is between 120 and 130 millimeters.

7. The intersomatic prosthesis according to claim 1, wherein the lower opening opens into the lower bearing wall at least over the entirety of the length of the central lower portion, such that the lower teeth comprise, on either side of the lower opening, a row of anterior lower teeth adjacent to the anterior lateral wall and a row of posterior lower teeth adjacent to the posterior lateral wall, and wherein the upper opening opens into the upper bearing wall at least over the entirety of the length of the central upper portion, such that the upper teeth comprise, on either side of the upper opening, a row of anterior upper teeth adjacent to the anterior lateral wall and a row of posterior upper teeth adjacent to the posterior lateral wall.

8. The intersomatic prosthesis according to claim 1, wherein the lower opening occupies between 50 and 75% of the surface area of the lower bearing wall, and the upper opening occupies between 50 and 75% of the surface area of the upper bearing wall.

9. The intersomatic prosthesis according to claim 1, wherein the right lower portion and the right upper portion consist of planar portions extending in respective convergent planes, inclined at a right angle of inclination smaller than 45 degrees, such that the right end has a height which decreases in a linear manner along the longitudinal direction starting from the central lower portion in the direction of the right end wall;

and wherein the left lower portion and the left upper portion consist of planar portions extending in respective convergent planes, inclined at a left angle of inclination equal to the right angle of inclination, such that the left end has a height which decreases in a linear manner along the longitudinal direction starting from the central lower portion in the direction of the left end wall.

10. The intersomatic prosthesis according to claim 9, wherein the right angle of inclination and the left angle of inclination are between 5 and 30 degrees.

11. The intersomatic prosthesis according to claim 1, wherein the right upper portion is provided with at least two projecting spikes, and the left upper portion is provided with at least two projecting spikes.

12. The intersomatic prosthesis according to claim 11, wherein the projecting spikes project over a height between 0.7 and 1.2 millimeters.

13. The intersomatic prosthesis according to claim 1, wherein the right end has a right slot opening both into the right end wall and into the two lateral walls and configured to cooperate with a gripping ancillary, and the left end has a left slot symmetrical to the right slot with respect to the sagittal plane and opening both into the left end wall and into the two lateral walls and configured to cooperate with the gripping ancillary.

14. The intersomatic prosthesis according to claim 13, wherein the right slot extends, from the right end wall, into the posterior lateral wall over a posterior length and extends into the anterior lateral wall over an anterior length which is equal to or smaller than the posterior length, and the left slot extends, from the left end wall, into the posterior lateral wall over a posterior length and extends into the anterior lateral wall over the anterior length.

15. The intersomatic prosthesis according to claim 1, wherein the anterior height is larger than or equal to the posterior height such that in the sagittal plane the upper bearing wall has a lateral inclination with respect to the lower bearing wall at a lateral angle of inclination between 0 and 30 degrees.

16. The intersomatic prosthesis according to claim 1, wherein the prosthesis body has four rounded edges at junctures between the lateral walls and the bearing walls, said rounded edges extending longitudinally from the right end wall up to the left end wall following the respective curvatures of the lateral walls.

17. The intersomatic prosthesis according to claim 1, comprising at least three markers made of a radiopaque material, with a right marker placed on the right end wall and a left marker placed on the left end wall asymmetrically to the right marker with respect to the sagittal plane, and with a central marker placed on one of the lateral walls in the sagittal plane.

18. The intersomatic prosthesis according to claim 1, wherein an internal bridge extends inside the inner space between the two lateral walls, wherein said internal bridge is shifted downwards with respect to the upper bearing wall and is shifted upwards with respect to the lower bearing wall.

19. The intersomatic prosthesis according to claim 1, wherein a height, measured between the upper bearing wall and the lower bearing wall, decreases along the longitudinal direction, starting from the sagittal plane up to the right end wall, by 60 to 80%, and symmetrically with respect to the sagittal plane, a height, measured between the upper bearing wall and the lower bearing wall, decreases along the longitudinal direction, starting from the sagittal plane up to the left end wall, by 60 to 80%.

* * * * *